United States Patent [19]

Clineschmidt

[11] Patent Number: 4,501,749

[45] Date of Patent: Feb. 26, 1985

[54] PERIPHERALLY SELECTIVE DOPAMINE ANTAGONISTS IN THE TREATMENT OF OCULAR HYPERTENSION

[75] Inventor: Bradley V. Clineschmidt, Jeffersonville, Pa.

[73] Assignee: Merck & Co., Inc., Rahway, N.J.

[21] Appl. No.: 547,188

[22] Filed: Oct. 31, 1983

[51] Int. Cl.³ .................... A61K 31/33; A61K 31/445
[52] U.S. Cl. ................................. 514/326; 514/320; 514/324; 514/913
[58] Field of Search ............................. 424/267, 244

[56] References Cited

U.S. PATENT DOCUMENTS 4,370,324  1/1983  Bernstein ............................ 424/330
4,412,999  11/1983  Remy et al. ......................... 424/267

FOREIGN PATENT DOCUMENTS 0005607  11/1979  European Pat. Off. ............ 424/267
1542514  3/1979  United Kingdom .

OTHER PUBLICATIONS

Langham, "The Intraocular Pressure Response to α and β Adrenergic Agonists in Normal and Glaucomatous Eyes", International Glaucoma Symposium (France), 1974.

Rosenbaum, "A Controlled Clinical Evaluation of Timolol in the Treatment of Patients with Elevated Intraocular Pressure", Glaucoma, vol. 1(1): 21-24, (1979).

Merck Index, 9th Edition, entry 6018, pp. 801-802, (1976).

Primary Examiner—Allen J. Robinson
Assistant Examiner—Joyce L. Morrison
Attorney, Agent, or Firm—William H. Nicholson

[57] ABSTRACT

Peripherally selective dopamine antagonists are useful in the treatment of ocular hypertension when administered topically to the eye.

2 Claims, No Drawings

PERIPHERALLY SELECTIVE DOPAMINE ANTAGONISTS IN THE TREATMENT OF OCULAR HYPERTENSION

SUMMARY OF THE INVENTION

This invention is concerned with the topical ophthalmic administration of peripherally selective dopamine antagonists for the treatment of abnormally elevated intraocular pressure. The peripheral dopamine antagonists contemplated for use in the novel ophthalmic formulations and method of treatment of this invention include certain esters of cyproheptadine-3-carboxylic acid described in U.S. Pat. No. 4,412,999, domperidone, (British patent No. 1,542,514), metoclopramide or the like.

The use of the peripherally selective dopamine antagonists reduces to a minimum the possibility of central nervous system effects such as concurrent tranquilization and ultimately tardive dyskinesia following the use of centrally active dopamine antagonists.

BACKGROUND OF THE INVENTION

Glaucoma is an ocular disorder associated with elevated ocular pressures which are too high for normal function and may result in irreversible loss of visual function. If untreated, glaucoma may eventually lead to blindness. Ocular hypertension, i.e., the condition of elevated intraocular pressure without optic nerve head damage or characteristic glaucomatous visual field defects, is now believed by many ophthalmologists to represent the earliest phase of glaucoma.

Many of the drugs formerly used to treat glaucoma proved not entirely satisfactory. Indeed, few advances were made in the treatment of glaucoma since pilocarpine and physostigmine were introduced. Only recently have clinicians noted that many β-adrenergic blocking agents are effective in reducing intraocular pressure. While many of these agents are effective in reducing intraocular pressure, they also have other characteristics, e.g. membrane stabilizing activity, that are not acceptable for chronic ocular use.

(S)-1-tert-butylamino-3-[(4-morpholino-1,2,5-thiadiazol-3-yl)oxy]-2-propanol, a β-adrenergic blocking agent, was found to reduce intraocular pressure and to be devoid of many unwanted side effects associated with pilocarpine and, in addition, to possess advantages over many other β-adrenergic blocking agents, e.g. to be devoid of local anesthetic properties, to have a long duration of activity, and to display minimal tolerance.

Carbonic anhydrase inhibitors are used to treat intraocular pressure by oral, intravenous or other systemic routes, and thereby have the distinct disadvantage of inhibiting carbonic anhydrase throughout the entire body. Such a gross disruption of a basic enzyme system is justified only during an acute attack of alarmingly elevated intraocular pressure, or when no other agent is effective. Despite the desirability of directing the carbonic anhydrase inhibitor only to the desired ophthalmic target tissue, no topically effective carbonic anhydrase inhibitors are available for clinical use. However, topically effective carbonic anhydrase inhibitors have been reported in European Patent Applications Nos. 70,239 and 79,269.

Now with the present invention there are provided novel ophthalmic formulations for the topical application of peripherally selective dopamine antagonists and a novel method of treating elevated intraocular pressure with those formulations.

DETAILED DESCRIPTION OF THE INVENTION

The novel formulations of this invention are adapted for topical administration to the eye such as a suspension, ointment, or as a solid insert. Formulations of these compounds may contain from 0.01 to 15% and especially 0.5% to 3% of medicament. Higher dosages as, for example, about 10%, or lower dosages can be employed provided the dose is effective in reducing or controlling elevated intraocular pressure. As a unit dosage from between 0.001 to 10.0 mg, preferably 0.005 to 2.0 mg, and especially 0.1 to 1.0 mg of the compound is generally applied to the human eye, generally on a daily basis in single or divided doses so long as the condition being treated exists.

These hereinbefore described dosage values are believed suitable for human patients and are based on the known and presently understood pharmacology of the compounds, and the action of other similar entities in the human eye. They reflect the best mode known. As with all medications, dosage requirements are variable and must be individualized on the basis of the disease and the response of the patient.

The pharmaceutical preparation which contains the active compound may be conveniently admixed with a non-toxic pharmaceutical organic carrier, or with a non-toxic pharmaceutical inorganic carrier. Typical of pharmaceutically acceptable carriers are, for example, water, mixtures of water and water-miscible solvents such as lower alkanols or aralkanols, vegetable oils, polyalkylene glycols, petroleum based jelly, ethyl cellulose, ethyl oleate, carboxymethylcellulose, polyvinylpyrrolidone, isopropyl myristate and other conventionally employed acceptable carriers. The pharmaceutical preparation may also contain non-toxic auxiliary substances such as emulsifying, preserving, wetting agents, bodying agents and the like, as for example, polyethylene glycols 200, 300, 400 and 600, carbowaxes 1,000, 1,500, 4,000, 6,000 and 10,000, antibacterial components such as quaternary ammonium compounds, phenylmercuric salts known to have cold sterilizing properties and which are non-injurious in use, thimerosal, methyl and propyl paraben, benzyl alcohol, phenylethanol, buffering ingredients such as sodium chloride, sodium borate, sodium acetate, gluconate buffers, and other conventional ingredients such as sorbitan monolaurate, triethanolamine oleate, polyoxyethylene sorbitan monopalmitylate, dioctyl sodium sulfosuccinate, monothioglycerol, thiosorbitol, ethylenediamine tetraacetic acid, and the like. Additionally, suitable ophthalmic vehicles can be used as carrier media for the present purpose including conventional phosphate buffer vehicle systems, isotonic boric acid vehicles, isotonic sodium chloride vehicles, isotonic sodium borate vehicles and the like.

The pharmaceutical preparation may also be in the form of a solid insert. While many patients find liquid medication to be entirely satisfactory, others may prefer a solid medicament that is topically applied to the eye, for example, a solid dosage form that is suitable for insertion into the cul-de-sac. To this end the active agent can be included with a non-bioerodible insert, i.e. one which after dispensing the drug remains essentially intact, or a bioerodible insert, i.e. one that either is soluble in lacrimal fluids, or otherwise disintegrates. While the insert employed is not critical and those disclosed in U.S. Pat. Nos. 3,630,200 Higuchi; 3,811,444 Heller et al.; 4,177,256 Michaels et al.; 3,868,445 Ryde et al.; 3,845,201 Haddad; 3,981,303 Higuchi; and 3,867,519 Michaels, are satisfactory; in general, however, an insert using a solid water soluble polymer as the carrier for the medicament is found preferable.

The polymer used to form the insert may be any water soluble non-toxic polymer, for example, cellulose derivatives such as methylcellulose, sodium carboxymethyl cellulose, or a hydroxy lower alkyl cellulose such as hydroxyethyl cellulose, hydroxypropyl cellulose, hydroxypropylmethyl cellulose and the like; acrylates such as polyacrylic acid salts, ethyl acrylates, polyacrylamides; natural products such as gelatin, alginates, pectins, tragacanth, karaya, chondrus, agar, acacia; the starch derivatives such as starch acetate, hydroxyethyl starch ethers, hydroxypropyl starch, as well as other synthetic derivatives such as polyvinyl alcohol, polyvinyl pyrrolidone, polyvinyl methyl ether, polyethylene oxide, neutralized carbopol and xanthan gum, and mixtures of said polymer.

Examples of peripherally selective dopamine antagonists useful as the active ingredient in the novel ophthalmic formulations and method of treatment of this invention are domperidone, metoclopramide and certain esters of cyproheptadine-3-carboxylix acid described in U.S. Pat. No. 4,412,999, the disclosure of which is incorporated herein by reference. These esters have structural formula:

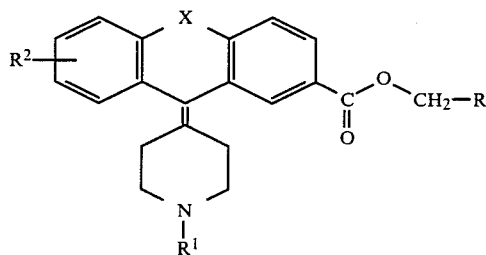

or a pharmaceutically acceptable salt thereof, wherein X is (1) —CH=CH—, (2) —CH$_2$—CH$_2$—, (3) —CH$_2$—O—, (4) —O—CH$_2$—, (5) —CH$_2$—S—, (6) —S—CH$_2$—, (7) —S—, or (8) —O—;
R is

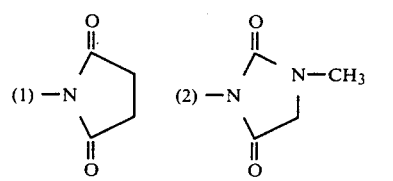

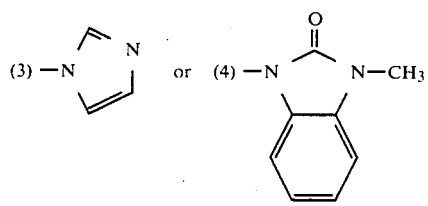

R$^1$ is (1) C$_{1-3}$ alkyl, or

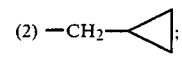

and R$^2$ is (1) hydrogen, (2) C$_{1-3}$ alkyl, or (3) fluoro.

In a preferred embodiment of the novel formulations of this invention X is —CH=CH—, —CH$_2$—CH$_2$—, or —S—; R is

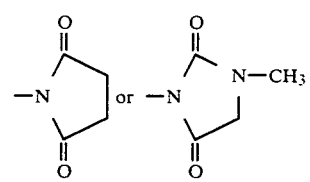

R$^1$ is —CH$_3$; and R$^2$ is hydrogen.

In an even more preferred embodiment X is —CH=CH—; R is

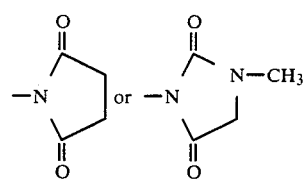

R$^1$ is —CH$_3$ and R$^2$ is hydrogen.

The compounds wherein X is —CH=CH— exist as dextrorotatory and levorotatory atropisomers and racemic mixtures thereof. Only the levorotatory enantiomers thereof are active in lowering intraocular pressure. Accordingly this invention contemplates the use of only those compounds with zero or negative optical rotation.

The pharmaceutically acceptable salts of the compounds are acid addition salts formed from a novel compound and an organic or inorganic acid recognized by the art as providing a pharmaceutically acceptable acid addition salt, such as hydrochloride, hydrobromide, dihydrogen phosphate, sulfate, citrate, pamoate, pyruvate, napsylate, isethionate, maleate, fumarate, or the like.

EXAMPLE 1

| Solution Composition | | |
|---|---|---|
| Domperidone | 1 mg. | 15 mg. |
| Monobasic sodium phosphate .2H$_2$O | 9.38 mg. | 6.10 mg. |
| Dibasic sodium phosphate .12H$_2$O | 28.48 mg. | 16.80 mg. |
| Benzalkonium chloride | 0.10 mg. | 0.10 mg. |
| Water for injection q.s. ad. | 1.0 ml | 1.0 ml. |

The sterile components are added to and suspended in sterile water. The pH of the suspension is adjusted to 6.8 sterilely and diluted to volume.

EXAMPLE 2

Metoclopromide: 5 mg.
petrolatum q.s. ad.: 1 gram
The active compound and the petroleum are aseptically combined.

EXAMPLE 3

(−)-(3-Methyl-2,5-dioxo-1-imidazolidinyl)-methyl 5-(1-methyl-4-piperidinylidene)-5H-dibenzo[a,d]cycloheptene-3-carboxylate: 1 mg.

Hydroxypropylcellulose q.s.: 12 mg.

Ophthalmic inserts are manufactured from compression molded films which are prepared on a Carver Press by subjecting the powdered mixture of the above ingredients to a compressional force of 12,000 lbs. (gauge) at 300° F. for one to four minutes. The film is cooled under pressure by having cold water circulate in the platen. Ophthalmic inserts are then individually cut from the film with a rod-shaped punch. Each insert is placed into a vial, which is then placed in a humidity cabinet (88% R.H. at 30° C.) for two to four days. After removal from the humidity cabinet, the vials are stoppered and then capped. The vials containing the hydrate insert are then autoclaved at 250° F. for ½ hour.

EXAMPLE 4

(−)-(2,5-Dioxo-2-Pyrrolidinyl)methyl 5-(1-methyl-4-piperidinylidene)-5H-dibenzo[a,d]cycloheptene-3-carboxylate: 1 mg.

Hydroxypropyl cellulose q.s. ad.: 12 mg.

Ophthalmic inserts are manufactured from a solvent cast film prepared by making a viscous solution of the powdered ingredients listed above using methanol as the solvent. The solution is placed on a Teflon plate and allowed to dry at ambient conditions. After drying, the film is placed in an 88% R. H. cabinet until it is pliable. Appropriately sized inserts are cut from the film.

EXAMPLE 5

(2,5-Dioxo-1-pyrrolidinyl)methyl 10,11-dihydro-5-(1-methyl-4-piperidinylidene)-5H-dibenzo[a,d]cycloheptene-3-carboxylate: 1 mg.

(Hydroxypropyl methyl cellulose q.s. ad.: 12 mg.

Ophthalmic inserts are manufactured from a solvent cast film which is prepared by making a viscous solution of the powdered blend of the above ingredients using a methanol/water solvent system (10 ml. methanol is added to 2.5 g. of the powdered blend), to which 11 ml. of water (in three divided portions) is added. The solution is placed on a Teflon plate and allowed to dry at ambient conditions. After drying, the film is placed in an 88% R. H. cabinet until it is pliable. Appropriately sized inserts are then cut from the film.

EXAMPLE 6

(2,5-Dioxo-1-Pyrrolidinyl)methyl 9-(1-methyl-4-piperidinylidene)-9H-thioxanthene-2-carboxylate: 1 mg.

Hydroxypropylmethyl cellulose q.s. ad.: 12 mg.

EXAMPLE 7

(−)-(2,5-Dioxo-1-Pyrrolidinyl)methyl 5-(1-methyl-4-piperidinylidene)-5H-dibenzo[a,d]cycloheptene-3-carboxylate: 0.1 mg.

Peanut oil q.s. ad.: 0.10 mg.

What is claimed is:

1. A method of treating glaucoma and ocular hypertension which comprises topical application to the eye of a patient in need of such treatment of an effective intraocular pressure lowering amount of a compound of structural formula I with zero or negative optical rotation:

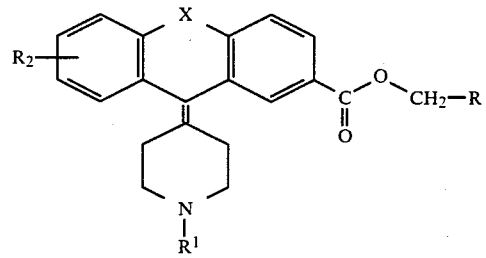

or a pharmaceutically acceptable salt thereof, wherein X is (1) —CH=CH—, (2) —CH$_2$—CH$_2$—, (3) —CH$_2$—O—, (4) —O—CH$_2$—, (5) —CH$_2$—S—, (6) —S—CH$_2$—, (7) —S—, or (8) —O—;

R is

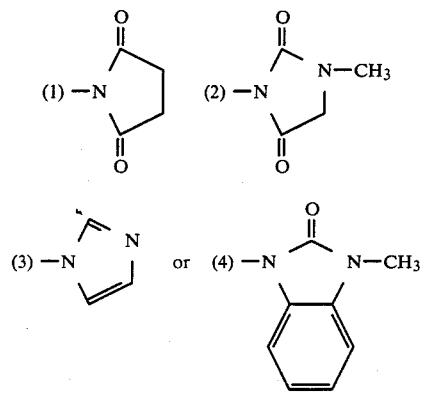

R$^1$ is (1) C$_{1-3}$ alkyl, or

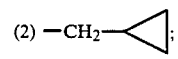

and R$^2$ is (1) hydrogen, (2) C$_{1-3}$ alkyl, or (3) fluoro.

2. The method of claim 1 wherein the compound is (−)-(3-methyl-2,5-dioxo-1-imidazolindinyl)methyl 5-(1-methyl-4-piperidinylidene-5H-dibenzo[a,d]cycloheptene-3-carboxylate.

* * * * *